United States Patent
Guillemet et al.

(10) Patent No.: US 9,239,310 B2
(45) Date of Patent: Jan. 19, 2016

(54) CAPACITIVE SENSOR INTEGRATED ONTO SEMICONDUCTOR CIRCUIT

(71) Applicant: MEAS FRANCE, Toulouse (FR)

(72) Inventors: Jean-Paul Guillemet, Labarthe sur Leze (FR); Predrag Drljaca, Neuchatel (CH); Daniel Beeler, Eschenbach (CH); Romuald Gallorini, Plaisance du Touch (FR); Vincent Ducere, Colomiers (FR)

(73) Assignee: MEAS FRANCE, Toulouse (FR)

( * ) Notice: Subject to any disclaimer, the term of this patent is extended or adjusted under 35 U.S.C. 154(b) by 0 days.

(21) Appl. No.: 14/152,085

(22) Filed: Jan. 10, 2014

(65) Prior Publication Data

US 2014/0197500 A1    Jul. 17, 2014

(30) Foreign Application Priority Data

Jan. 11, 2013 (EP) .................................... 13305026

(51) Int. Cl.
*H01L 21/00* (2006.01)
*G01N 27/403* (2006.01)
*G01N 27/22* (2006.01)

(52) U.S. Cl.
CPC ............ *G01N 27/226* (2013.01); *G01N 27/223* (2013.01); *G01N 27/227* (2013.01); *G01N 27/228* (2013.01)

(58) Field of Classification Search
CPC . G01N 27/226; G01N 27/227; G01N 27/223; G01N 27/228; H01L 41/1132
See application file for complete search history.

(56) References Cited

U.S. PATENT DOCUMENTS

| | | | |
|---|---|---|---|
| 4,603,372 A * | 7/1986 | Abadie et al. | 361/286 |
| 2004/0008471 A1 | 1/2004 | Davis et al. | |
| 2007/0264741 A1 | 11/2007 | Patel et al. | |
| 2012/0168882 A1* | 7/2012 | Cherian et al. | 257/414 |

FOREIGN PATENT DOCUMENTS

EP    2420826 A    2/2012

OTHER PUBLICATIONS

International Search Report dated Mar. 25, 2014 for related International Application No. PCT/EP2014/050097.
Fenner, Ralph and Zdankiewicz, Edward, "Micromachined Water Vapor Sensors: a Review of Sensing Technologies", IEEE Sensors Journal, vol. 1, No. 4, pp. 309-317, Dec. 2001.

(Continued)

*Primary Examiner* — Su C Kim
(74) *Attorney, Agent, or Firm* — Howard IP Law Group, PC

(57) ABSTRACT

There is disclosed a capacitive sensor on a passivation layer of a semiconductor circuit such as an ASIC, and a method for manufacturing such sensor. The system and method may comprise: forming a bottom electrode layer and landing pad on a portion of the passivation layer located over active circuitry of the ASIC; forming a gas sensitive layer onto the bottom electrode layer and the landing pad; creating a via through the gas sensitive layer to expose a portion of the landing pad; forming a top electrode layer onto the gas sensitive layer, wherein the top electrode layer completely overlays a surface area of the bottom electrode layer, and wherein the forming process for the top electrode layer deposits a portion of the top electrode layer into the via hole, thereby forming an electrical connection between the top electrode layer and the landing pad.

20 Claims, 7 Drawing Sheets

(56) References Cited

OTHER PUBLICATIONS

Plum, T. J. et al. "Design of a MEMS Capacitive Chemical Sensor Based on Polymer Swelling", IEEE, pp. 49-50, 2006.

Lazarus, N. and Fedder, G. K., "Integrated vertical parallel-plate capacitive humidity sensor", Journal of Micromechanics and Microengineering, 21, pp. 1-9, May 2011.

* cited by examiner

CAPACITIVE SENSOR INTEGRATED ONTO SEMICONDUCTOR CIRCUIT

FIELD OF THE INVENTION

The present invention relates generally to capacitive gas sensors constructed directly on top of the outermost passivation layer of a semiconductor circuit.

CROSS REFERENCE TO RELATED APPLICATIONS

This application claims priority to co-pending European patent application Serial No. 13 305 026.0, filed Jan. 11, 2013, pursuant to 35 U.S.C. §119(a)-(d), the entire contents of which is hereby incorporated herein by reference for all purposes.

BACKGROUND OF THE INVENTION

Capacitive gas sensors are known in the art, a particular example being in the measurement of water vapor (relative humidity). There are a number of configurations associated with these sensors. One configuration uses interdigitated coplanar electrodes of opposite polarity covered by a gas sensitive material in which increasing gas concentration causes an increase in the dielectric constant of such material thereby increasing the dielectric coupling between planar electrodes and thereby increasing the effective capacitance between the electrodes. In the case of the interdigitated electrodes, both electrodes are underneath the top surface of the gas sensitive material, and the dielectric coupling between the planar electrodes occurs by field fringing effects.

Another configuration employs parallel plate-like electrodes with a layer of gas sensitive material between them such that changing gas concentration changes the dielectric constant of the gas sensitive material and changes the capacitance of the parallel plate capacitor. A parallel plate configuration described in FR2750494 (U.S. Pat. No. 6,450,026) has a top electrode comprised of a highly porous conducting polymer that allows the diffusion of the selected gas through the electrode and into the gas sensitive material. This top electrode material is processed so that it is tightly bonded to the gas sensitive material and is chemically inert and environmentally robust. FR2750494 and U.S. Pat. No. 6,450,026 are incorporated by reference herein in their entirety.

The capacitance of a capacitive gas sensor is a function of gas concentration, and the capacitance is measured by associated electronics capable of exciting the sensor electrically. The cost of manufacture of the capacitive gas sensors is associated with the physical size of the sensor and the associated electronics, hence it is desirable to provide capacitive gas sensors as small as possible while still achieving desired accuracy and signal to noise ratio. As the size of gas sensitive capacitors is reduced, the gas sensitive capacitors become increasingly susceptible to signal degradation associated with stray capacitances, including parasitic capacitances found in interconnections and in the associated electronics. One way to reduce the effects of parasitic capacitances when using smaller capacitors is to locate the associated electronics as physically close to the sensor as possible.

Along with reducing the size and therefore the cost of manufacture of the capacitive gas sensors, it is desirable to decrease the size and cost of the associated electronics. Reduced cost of manufacture of the associated electronics can be achieved through the use of application specific integrated circuits (ASICS) which provide all necessary functionality in a small low cost configuration.

There are commercial devices available in which interdigitated coplanar capacitor electrodes are disposed on top of a section of an ASIC and a gas sensitive material layer is disposed on top of the coplanar sensor electrodes to form a gas sensor. This configuration for ASICs with interdigitated capacitor electrodes has a disadvantage in that if the interdigitated capacitor electrodes are directly over active circuitry in the ASIC, coupling and interference is likely. This results in a need for a larger silicon area to accommodate the sensor electrodes so they are not over active circuitry. Notably, the interdigitated electrodes cannot be shielded from the circuitry-induced stray coupling signals by the addition of a conductive layer intermediate the electrodes and underneath because such a conductive layer would significantly increase the baseline capacitive coupling between the interdigitated sensing electrodes. Since the signal generated by changing gas concentrations in the gas sensitive layer is measured as a changing percentage of capacitance, increasing the baseline capacitance will lower the sensitivity of the device. Another drawback to ASICs with interdigitated electrodes is the undesirable sensitivity of the inter electrode capacitance to foreign material on the top of the gas sensitive material layer. For example, water droplets or small metal particles on the surface of the gas sensitive material layer can significantly alter the dielectric coupling between the electrodes by distorting fringing electric fields generated by the electrodes.

An alternative device has two separate chips: one chip has a gas sensing capacitor built atop an appropriate substrate and the second chip suitable circuitry. This two chip solution has the advantage of decoupling the production yields, the processes, and the substrate materials used to produce each part. However, these chips must be electrically interconnected using flip chip or wire bonding technology, both of which affect the behavior of the sensing capacitor. Further the cost of electrical and mechanical packaging is greater than the vertically integrated configuration.

Therefore, there is a need for a smaller and more effective capacitive gas sensor constructed directly on top of an appropriate semiconductor circuitry.

SUMMARY OF THE INVENTION

An embodiment of the present invention relates to a gas sensor assembly comprised of a parallel plate capacitive gas sensor which is constructed directly on top of the passivated surface of a standard semiconductor gas sensor ASIC. The configuration provides the benefits of the parallel plate sensor configuration while allowing the smallest possible sensor size.

An object of the present invention is to produce a capacitive sensor for measuring gas atop a semiconductor circuit, whereby manufacture thereof is simplified.

In addition to sensors to be used as gas sensors, the present invention relates to the manufacturing method for these sensors. In a preferred embodiment, this method relates to the successive stacking or formation of a thin metal layer, a gas sensitive layer, and a porous top electrode.

A method for manufacturing a capacitive sensor on a passivation layer of a semiconductor circuit may comprise: the deposition of a metal layer atop the passivation layer covering the circuitry, the metallization layer patterned to create a bottom electrode, a first trace connecting the bottom electrode to a first bond pad, a landing pad, and a second trace connecting the landing pad to a second bond pad, the bottom electrode being positioned so that it is located over a portion of the semiconductor circuit which contains active circuitry; depositing a gas sensitive layer onto the bottom electrode and the landing pad; creating a via hole through the gas sensitive layer to expose the landing pad; and depositing a porous conductive electrode onto the gas sensitive layer to form a top electrode electrically connected to the landing pad through the via hole, wherein a portion of the top electrode completely overlays a surface area of the bottom electrode and the top electrode connects to the landing pad.

In an embodiment, a method for manufacturing a capacitive sensor on a passivation layer of an ASIC (510) may comprise: forming a bottom electrode layer and landing pad (520) on a portion of the passivation layer located over active circuitry of the ASIC; forming a gas sensitive layer (530) onto the bottom electrode layer and the landing pad; creating a via hole (540) through the gas sensitive layer to the landing pad; forming a top electrode layer (550) onto the gas sensitive layer, wherein the top electrode layer completely overlays a surface area of the bottom electrode layer, and wherein the forming process for the top electrode layer includes filling the via hole with electrically conductive material, thereby forming an electrical connection between the top electrode layer and the landing pad.

In an embodiment, the process used for forming the bottom electrode layer and landing pad from a metal layer deposited on the passivation layer may comprise a photolithographic process, a photolithographic resist process, or a wet etching process. A spin coating process may be used for forming a gas sensitive layer onto the bottom electrode layer and the landing pad. In an embodiment, the method may further comprise applying a pattern to the gas sensitive layer using a photolithographic technique followed by dry or wet etching processes. The process used for forming the porous top electrode layer onto the gas sensitive layer may comprise screen printing, stencil printing, pad printing, ink jetting, or spin coating. In an embodiment, the method may further comprise forming a molding compound onto the top electrode and the ASIC such that an opening in the molding compound exposes the top electrode to the ambient environment and such that the molding compound covers at least 0.1 mm of the gas sensitive material along all mold compound edges around the opening.

A gas sensor may comprise: a semiconductor circuit (200) having a top passivation layer (210); a metal bottom electrode (310) on the passivation layer (210) of the semiconductor circuit (200), wherein the bottom electrode (310) is located over an area of the semiconductor circuit that contains active circuitry, a metal landing pad (330) on the passivation layer (210) and electrically separate from the bottom electrode (310); a gas sensitive layer (340) on the metal bottom electrode (310) and metal landing pad (330), the gas sensitive layer (340) having a via (350) defined therethrough; a porous top electrode (320) on the gas sensitive layer (340), wherein an area formed by the porous top electrode (320) completely overlays an area formed by the metal bottom electrode (310), and wherein the porous top electrode (320) is electrically connected to the landing pad (330) through the via (350) in the gas sensitive layer (340); and a first metal trace (390) connecting the metal bottom electrode (310) to a first bond pad (380) and a second metal trace (370) connecting the landing pad (330) to a second bond pad (360). The bottom electrode, landing pad and both connecting traces may be patterned from the same metal layer (for example, by selective patterning). In an embodiment, the semiconductor circuit measures the capacitance of the gas sensitive layer by applying a signal to the metal bottom electrode (310) and measuring the charge displaced by the capacitor through the top electrode.

In an embodiment, the gas sensor layer (340) covers the first metal trace (390) and second metal trace (370), thereby preventing an electrical short circuit between the porous top electrode (320) and the metal bottom electrode (310) which may be caused by the process used to deposit the top electrode. In another embodiment, the gas sensor may further comprise a mold compound (400) adjacent the porous top electrode (320), the mold compound (400) having an opening (410) for exposing the porous top electrode (320) to the ambient environment, and wherein each side of the opening (410) in the mold compound overlays at least 0.1 mm of the gas sensitive layer (340). In the gas sensor, an area of the porous top electrode (320) may be larger than an area of the bottom electrode (310), thereby enabling the porous top electrode (320) to completely overlay the bottom electrode (310) even if they are misaligned.

DETAILED DESCRIPTION

Reference will now be made in detail to the present exemplary embodiments of the invention, examples of which are illustrated in the accompanying drawings.

Figure 1A:
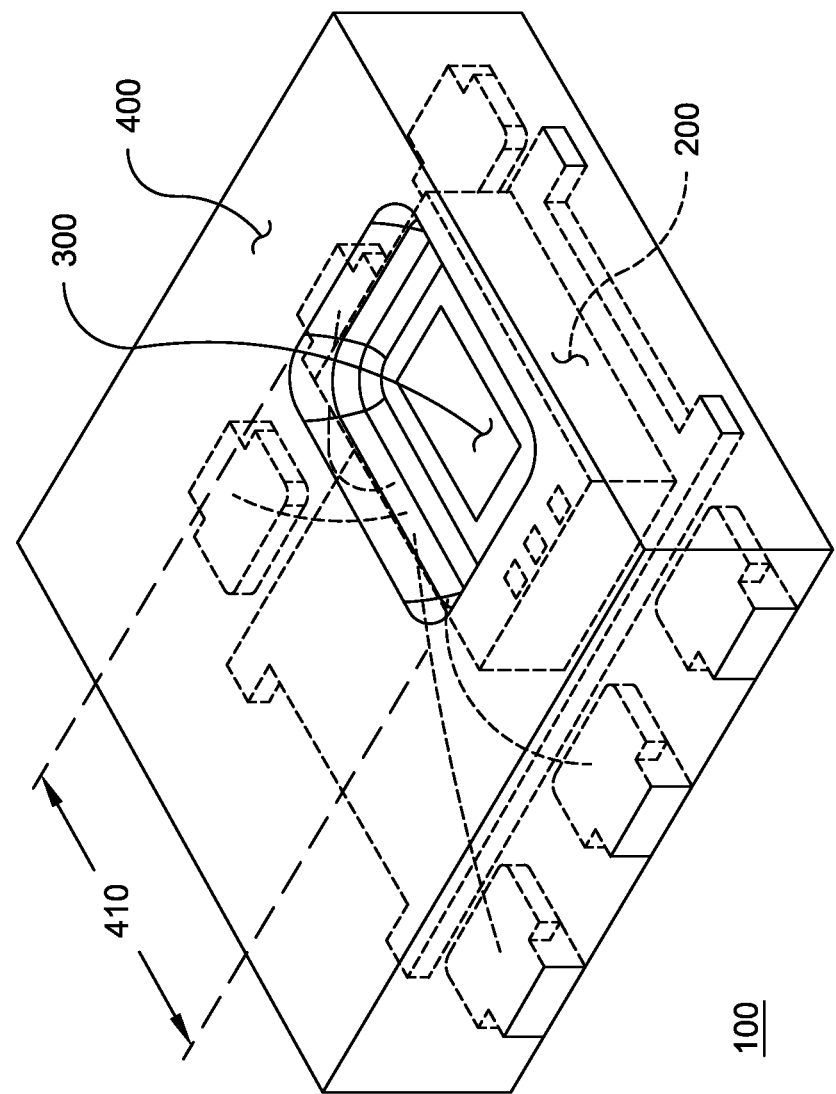
FIG. 1a shows a perspective view of an exemplary embodiment of a capacitive sensor integrated onto a semiconductor circuit including an over-molding compound.

FIG. 1a shows a perspective view of an exemplary embodiment of a gas sensor integrated onto a semiconductor circuit including a molding compound. In particular, FIG. 1a shows a gas sensor 100 which includes an ASIC (application specific integrated circuit) 200, a parallel plate capacitive sensor 300 on the ASIC 200, and a molding compound 400 over the gas sensor 100. The molding compound 400 includes an opening 410, which exposes the capacitive sensor 300 to the ambient environment so that it may make a reading of the condition it is designed to sense.

Figure 1B:
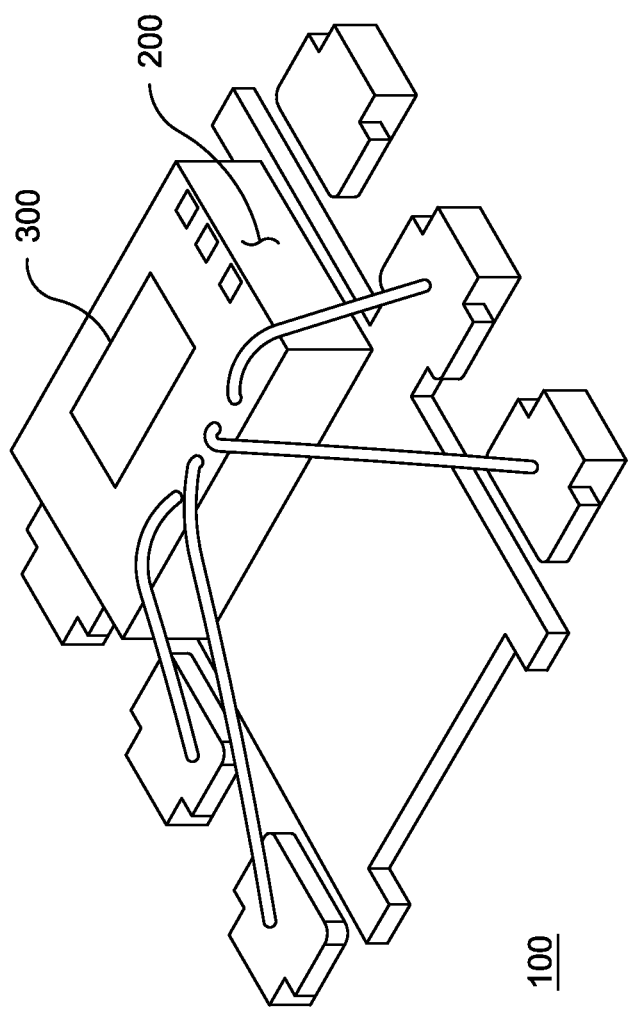
FIG. 1b shows a perspective view of an exemplary embodiment of a capacitive sensor integrated onto a semiconductor circuit, without an over-molding compound.

FIG. 1b shows an isometric view of the sensor 100 of FIG. 1a without the molding compound 400. The sensor 300 is shown roughly centered on top of the ASIC 200 to illustrate one embodiment of the device.

Figure 1C:
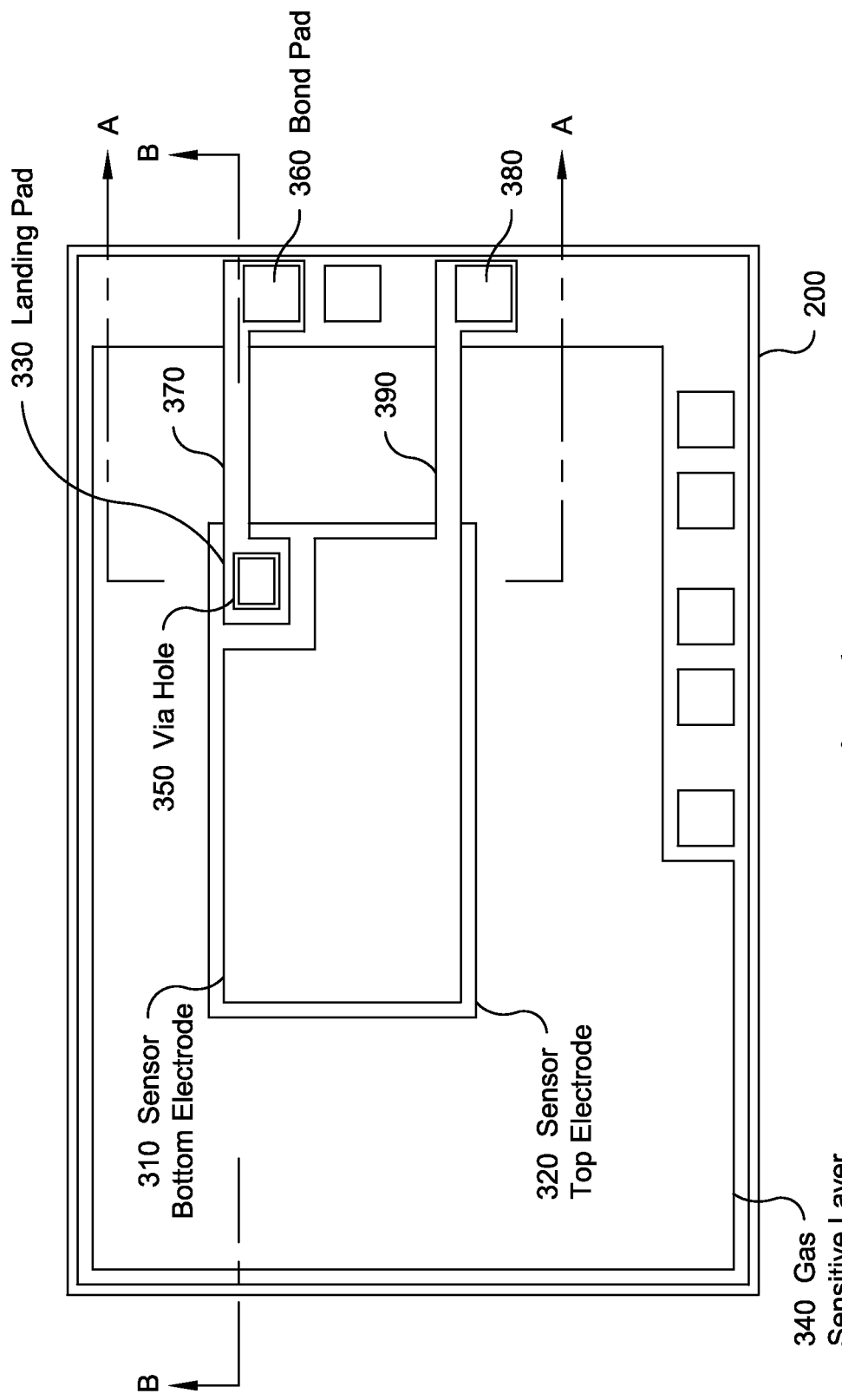
FIG. 1c shows a top view of the exemplary embodiment of an ASIC with a capacitive sensor integrated onto it, including the alignment of the bottom electrode, landing pad, via hole, and the interconnection of the bottom electrode and landing pad to their respective bond pads.

FIG. 1c shows a perspective view of an exemplary embodiment of the ASIC 200 with a sensor 300 integrated onto it. The molding compound 400 is not shown for clarity. The bottom electrode 310 may be formed using high precision semiconductor lithographic processes and in an embodiment may be comprised of a thin metal layer. In one non-limiting embodiment, the bottom electrode may be formed of Au with a TiW adhesion/barrier layer. The bottom electrode may be located above the active circuitry of the semiconductor circuit or ASIC, which results in a more compact design than sensors with interdigitated electrodes which are not placed atop active circuitry.

The porous top electrode 320 fully overlays the bottom electrode. The term overlay is used herein in the sense that the footprint or area of the top electrode fully overlaps the footprint of the bottom electrode forming essentially a parallel plate capacitor, but does imply contact between the top and bottom electrodes. In an embodiment, the top electrode is a porous electrode. The term "porous" is used herein the sense of not being totally impervious to the gases of interest. Examples of porous electrodes useful for carrying out embodiments of the present invention include but are not limited to film based porous electrodes, organic binders filled with platinum or carbon particles, and the like, by way of non-limiting example only.

The top electrode 320 is fabricated using a process to provide favorable porosity and adhesion, this process being generally less dimensionally accurate than those used to photolithographically image metal electrodes on semiconductor wafers as in the bottom electrode. For given dielectric properties and thickness of the gas sensing material, the baseline capacitance of the capacitive sensor is determined by the overlay of the bottom and top electrodes. In one non-limiting embodiment, the capacitance may be between about 1.5 pF and about 10 pF capacitance, however, this is exemplary only and various other ranges may be used (e.g. a range of about 0.2 pF to about 20 pF) depending on the requirements of the particular application. To eliminate the unavoidable variance in capacitance that would result from using top and bottom electrodes of identical size and the positioning and geometric tolerances of the deposition processes, in an embodiment the top electrode 320 may have a surface area larger than the surface area of the bottom electrode 310 as shown in FIG. 1c. In this way, complete overlay of the top electrode over the bottom electrode may be ensured and as a result the capacitance of the sensor will be consistent even if there is misalignment of the top electrode. The capacitance will be consistent as long as the misalignment does not cause the top electrode to no longer fully cover the bottom electrode.

FIG. 1c also shows bond pads 360 and 380 and metal traces 370 and 390. In the embodiment shown, bond pad 360 is electrically connected to the landing pad (which is connected to the top electrode) by metal trace 370. Similarly, bond pad 380 is electrically connected to the bottom electrode by metal trace 390. When a metal bottom layer is formed on the passivation layer of the ASIC, it is formed so that the electrode portion of the bottom layer makes contact with metal trace 370 and the landing pad portion of the bottom layer makes contact with metal trace 390. As will be understood, the bond pads are features that are designed as part of the ASIC so that a gas sensor can later be fabricated onto the ASIC. As will further be understood, bond pads 360 and 380 are electrically connected to the circuitry of the ASIC that determines the condition (such as a gas) being sensed. The ASIC or semiconductor circuit may also include output leads (not shown) that provide a signal with data indicative of the detected concentration of gas. As noted, the semiconductor circuit measures the capacitance of the gas sensitive layer by applying a signal to the metal bottom electrode (310) and measuring the charge displaced by the capacitor through the top electrode. The measurement is then used by the ASIC or semiconductor circuit to determine the condition being sensed.

Figure 2:
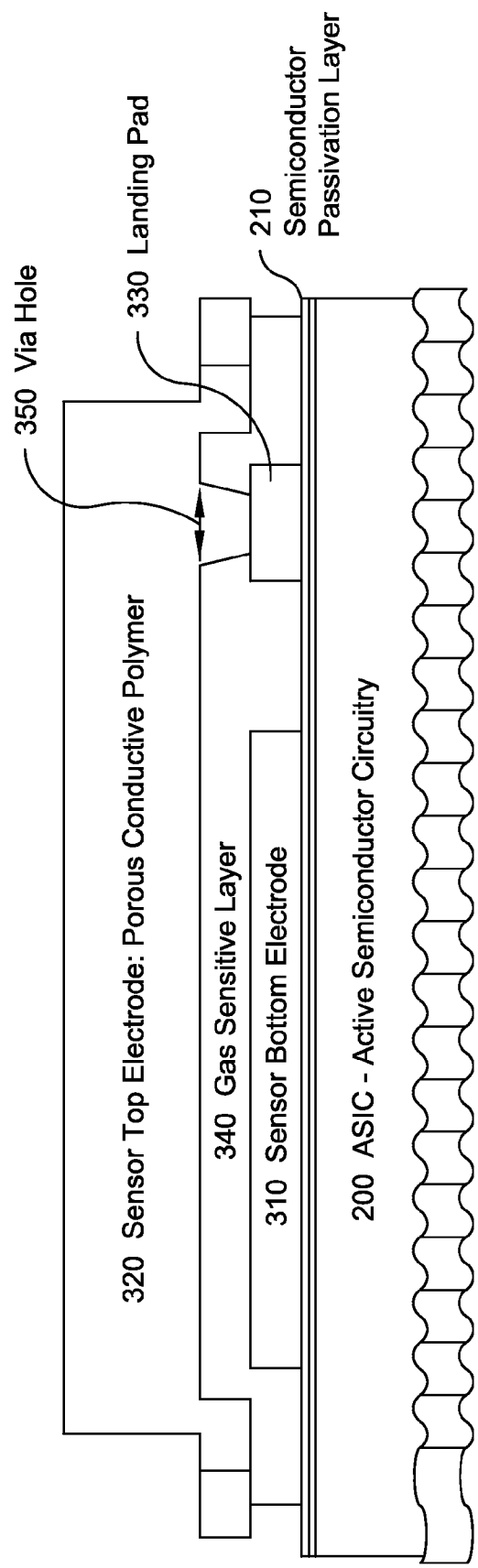
FIG. 2 shows a partial cross sectional view taken through A-A of FIG. 1c of the width of the short side of the ASIC configuration of FIG. 1c, including the top electrode covering the bottom electrode and making contact through the via hole in the gas sensitive material layer.

FIG. 2 shows a partial cross sectional view A-A of the width of the shorter side of ASIC 200 of FIG. 1c. In the embodiment of FIG. 2, the top electrode 320 completely covers and overlays the bottom electrode 310 and makes connection to landing pad 330 for electrical interconnection of the top electrode 320 to the semiconductor circuitry. The gas sensing material layer 340 has defined therein an opening or via 350 filled with conductive material through which electrical contact is made between the top electrode 320 and the landing pad 330. The top electrode deposition process should ensure the top electrode 320 makes a reliable electrical interconnection to the landing pad 330 through the via 350. The gas sensing material 340 may be a dielectric material. In one non-limiting embodiment, the dielectric material may be a polymeric material such as a polymer film having a thickness of about 2 micrometers (microns). By way of further non-limiting example, for the gas sensitive material layer a polyimide (organic polymer) may be used, as is well known and in commercial use for humidity sensing. Still further, it is understood that gas sensitive polymer materials are known in the art and thus a further description is omitted herein for the sake of brevity.

Figure 3:
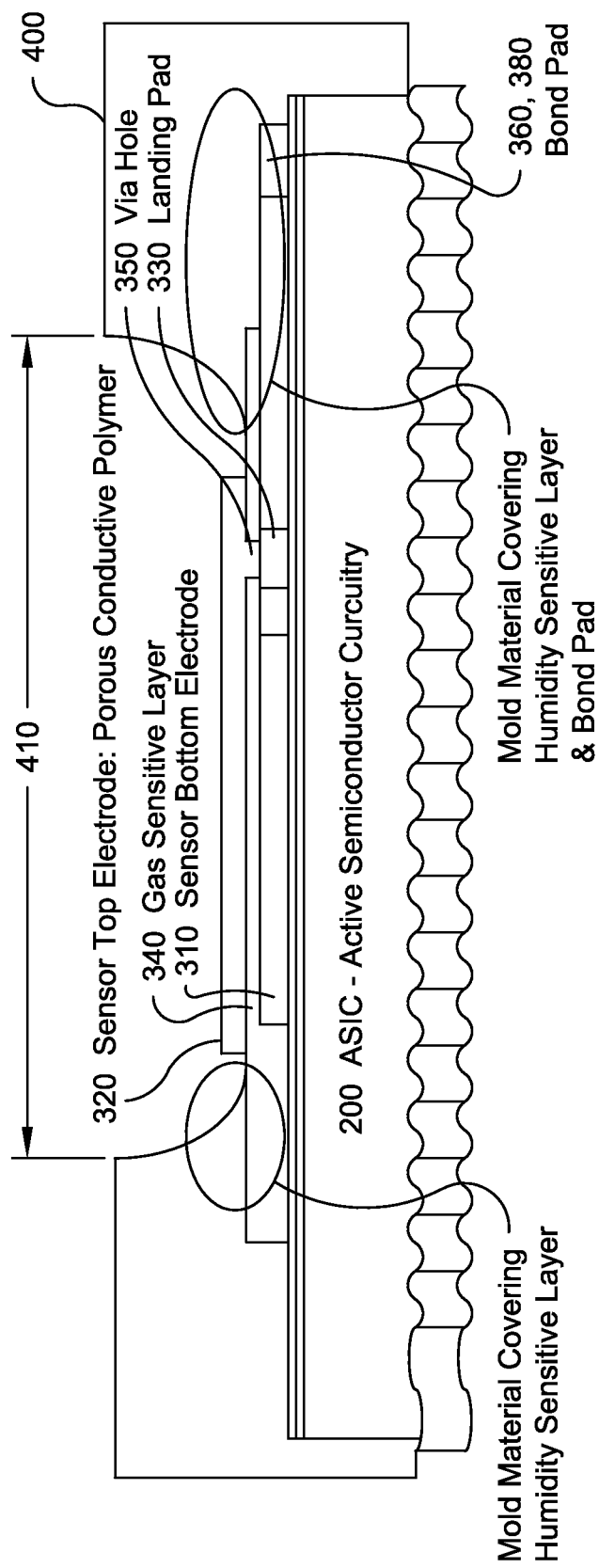
FIG. 3 shows a cross sectional lengthwise view taken through B-B of FIG. 1c of the long side of the ASIC configuration of FIG. 1c, including the overlap of the die packaging material over the connection pads for the capacitor connections.

FIG. 3 shows a cross sectional lengthwise view B-B of the longer side of ASIC 200 of FIG. 1c. This view shows the overlap of the packaging molding compound 400 over bond pads 360 and 380 used to interconnect the top 320 and bottom 310 electrodes to the ASIC circuitry, respectively. In an embodiment, the molding compound 400 covers the capacitor interconnection pads by at least 0.1 mm in order to ensure that small changes in the molding compound caused by the gas of interest being measured do not affect the dielectric coupling between the sensing capacitor connection traces or connection pads.

Figure 4:
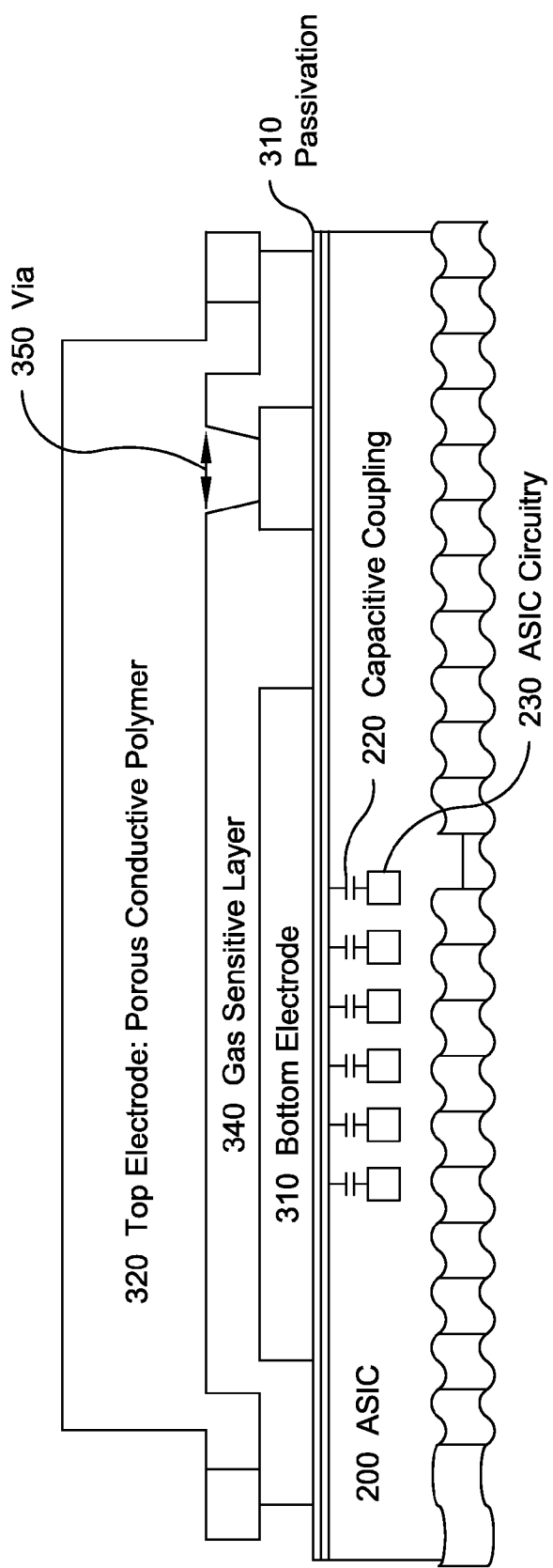
FIG. 4 shows a partial cross sectional view taken through A-A of FIG. 1c of the width of the short side of the ASIC configuration of FIG. 1c, including undesired parasitic capacitive coupling from the underlying circuitry to the bottom electrode.

FIG. 4 shows a partial cross sectional view A-A of the width of the ASIC 200 of FIG. 1c. FIG. 4 is similar to FIG. 2 except that it also shows how traces in the active circuitry underneath the semiconductor passivation layer can capacitively couple to the bottom electrode. The capacitive coupling is represented by the capacitor symbols 220 shown in the ASIC 200 that connect to ASIC circuitry 230.

In an embodiment, the sensor on the ASIC is a capacitive humidity sensor. The placement of a capacitive gas sensor directly atop active circuitry creates unintended parasitic capacitive coupling from the underlying circuitry to the bottom electrode of the capacitor as shown in FIG. 4. Because the change in capacitance with gas concentration is small relative to capacitance of the gas sensitive material at zero concentration, the accuracy of the sensor charge displacement measurement can be affected by this additional parasitic capacitive coupling. Further, the coupling may not be predictable or easily modeled using traditional circuitry modeling tools, as the circuitry beneath the bottom electrode is not in any way constrained by the presence of the gas sensing capacitor. In order to avoid the deleterious effects of these parasitic connections, in embodiments of the current invention the bottom electrode is driven by a low impedance voltage of known level, and the charge displaced by the sensing capacitor (a portion of which is due to the gas concentration) as a result of this applied voltage is measured using the top electrode. The voltage on the bottom electrode of the sensing capacitor, and therefore the charge displaced from the sensing capacitor, are unaffected by the parasitic capacitive coupling to any circuitry below the semiconductor passivation surface.

In order to reduce the cost and increase the reliability of the resulting sensor assembly, it is important that the processing associated with the gas sensing capacitor and its insulation and interconnection not damage the underlying circuitry. The semiconductor circuitry in the exemplary embodiment is produced using standard and highly cost effective CMOS design and fabrication ground rules and can be built on the largest wafers appropriate for the application (200 mm or 300 mm diameter silicon wafers, for example). This fabrication processing produces wafers that have exposed electrical interconnection bonding and testing pads, with the majority of the exposed top surface and all interconnection circuitry covered in a silicon nitride or silicon dioxide or similar passivation layer. In the current invention it is intended that the capacitive gas sensor be built directly atop this external passivation layer.

The steps in the fabrication of the capacitor and associated traces and packaging material according to an aspect of the present invention are conducted at sufficiently low temperatures to avoid damaging, or otherwise deleteriously affecting the performance or reliability of the underlying active semiconductor circuitry. The bottom electrode and the landing pad for the top electrode are fabricated using standard, low risk, low cost photolithographic processes such as PVD sputtering or evaporation, photolithographic resist imaging including develop and strip, and wet etching. The gas sensitive material and the porous top electrode do not damage materials typically exposed on the surface of a wafer at the conclusion of standard CMOS processing, including silicon nitride, silicon dioxide, aluminum, or silicon itself. The gas sensitive layer can be deposited using typical wafer processing techniques such as spin coating and baking, and the material may be patterned using photolithographic techniques similar to those use in the processing or semiconductor polymers (including photoresists and polyimides). The porous top electrode material may be deposited using a number of low temperature techniques including stencil printing, pad printing, ink jetting, or spin coating. The curing or baking temperatures required in all post CMOS processes are kept below temperatures which would cause harm to the underlying circuitry.

Figure 5:
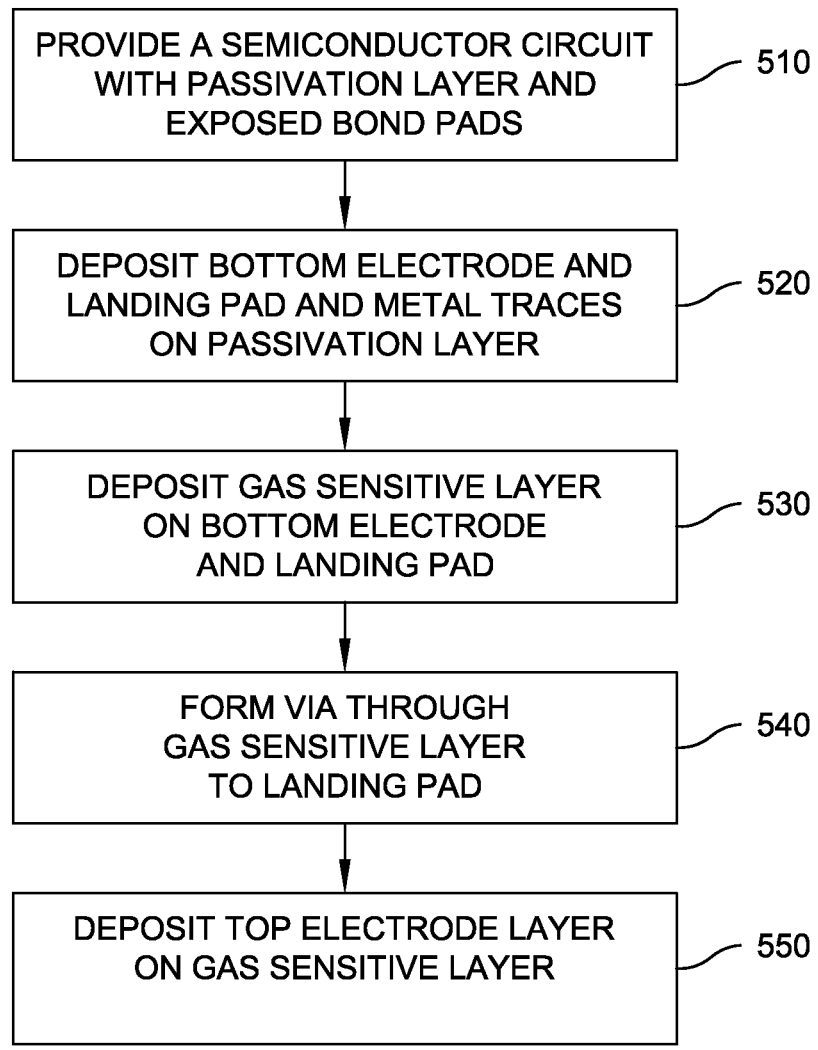
FIG. 5 is a flowchart of a process for manufacturing semiconductor circuits with an integrated gas sensor according to an embodiment of the invention.

In an embodiment, a semiconductor circuit (such as an ASIC) having an integrated gas sensor may be constructed using a method that uses low temperatures that prevent damage to the semiconductor circuit. Referring now to FIG. 5, in conjunction with FIGS. 2 and 3, there is shown a simplified logic flow chart or diagram 500 illustrating processing steps according to aspects of the disclosure. A semiconductor circuit such as an ASIC is provided in block 510. The semiconductor circuit may include a passivation layer (210) on top, as well as exposed bond pads (360 and 380). At block 520, a bottom electrode layer (310) and a landing pad (330) and metal traces (370 and 390) which are used to electrically connect the top (320) and bottom (310) electrodes of the gas sensor to the ASIC circuitry, are formed on the passivation layer (210). At block 530, the gas sensitive layer (340) may be formed. In one configuration, the metal traces used to connect the bottom electrode and the landing pad to their respective bond pads are created from the same metal layer by selective patterning. The gas sensitive layer (340) may be a dielectric such as a polymer. At block 540, a via or hole (350) is formed in the gas sensitive layer (340) using photolithographic patterning techniques. At block 550, the top electrode layer (320) is formed onto the gas sensitive layer (340) using low temperature techniques such as screen printing, stencil printing, pad printing, ink jetting, or spin coating. Deposition of the top electrode layer creates an electrical contact through via 350 to the landing pad 330. In one non-limiting example, the polymer material of the gas sensor may require curing, and as such the structure may be baked at an appropriate temperature for a given duration.

While the foregoing describes exemplary embodiments and implementations, it will be apparent to those skilled in the art that various modifications and variations can be made to the present invention without departing from the spirit and scope of the invention.

What is claimed is:

1. A method for manufacturing a capacitive sensor on a passivation layer of a semiconductor circuit, the passivation layer having openings which expose a first bond pad and a second bond pad comprising:
   forming a metal layer onto the passivation layer and patterning the metal layer to form a bottom electrode and landing pad and metal traces connecting the bottom electrode and the landing pad to their respective bond pads, the bottom electrode being positioned so that it is located over a portion of the semiconductor circuit with active circuitry;
   forming a gas sensitive layer onto the bottom electrode and the landing pad;
   creating a via through the gas sensitive layer to the landing pad;
   forming a porous top electrode onto the gas sensitive layer electrically connected to the landing pad through the via, wherein a portion of the top electrode completely overlays the surface area of the bottom electrode and an other portion of the top electrode is in contact with the landing pad.

2. The method of claim 1, further comprising forming a molding compound onto the top electrode and the semiconductor circuit such that an opening in the molding compound exposes the top electrode to an ambient environment and such that the molding compound covers at least 0.1 mm of the gas sensitive layer along all mold compound edges around the opening.

3. The method of claim 1, wherein the porous top electrode comprises a top surface exposed to an ambient environment.

4. The method of claim 1, wherein the semiconductor circuit is configured to measure a capacitance of the gas sensitive layer by applying a voltage to the bottom electrode and measuring a charge displaced by the capacitance through the porous top electrode.

5. A gas sensor comprising:
   a semiconductor circuit having a top passivation layer;
   a metal bottom electrode on the top passivation layer of the semiconductor circuit, wherein said metal bottom electrode is located over an area of the semiconductor circuit that contains active circuitry,
   a metal landing pad on the passivation layer and electrically separate from the metal bottom electrode;
   a gas sensitive layer on the metal bottom electrode and the metal landing pad, the gas sensitive layer including a via hole exposing a portion of the metal landing pad;
   a porous top electrode on the gas sensitive layer, wherein an area formed by the porous top electrode completely overlays an area formed by the metal bottom electrode, and wherein the porous top electrode is electrically connected to the metal landing pad through the via hole in the gas sensitive layer; and a first metal trace between the metal bottom electrode and a first bond pad and a second metal trace between the metal landing pad and a second bond pad;

wherein the semiconductor circuit measures a capacitance of the gas sensitive layer by applying a signal to the metal bottom electrode and measuring a charge displaced by the capacitance through the porous top electrode.

6. The gas sensor of claim 5, wherein the gas sensitive layer covers the first metal trace and the second metal trace, thereby preventing an electrical short circuit between the porous top electrode and the metal bottom electrode.

7. The gas sensor of claim 5, further comprising a mold compound adjacent the porous top electrode, the mold compound having an opening for exposing the porous top electrode to an ambient environment.

8. The gas sensor of claim 7, wherein each side of the opening in the mold compound overlays at least 0.1 mm of the gas sensitive layer.

9. The gas sensor of claim 5, wherein an area of the porous top electrode is larger than an area of the metal bottom electrode, thereby enabling the porous top electrode to completely overlay the metal bottom electrode even if they are misaligned.

10. The gas sensor of claim 5, wherein the porous top electrode comprises a top surface exposed to an ambient environment.

11. The gas sensor of claim 5, further comprising output leads in communication with the semiconductor circuit for providing a signal with data indicative of a detected concentration of gas.

12. The gas sensor of claim 11, wherein the signal comprises data indicative of a detected humidity.

13. The gas sensor of claim 12, wherein the gas sensitive layer is a polyimide responsive to humidity.

14. A gas sensor comprising:

an integrated circuit capable of measuring capacitance of a parallel plate capacitive sensor by applying a voltage and measuring a resulting displaced charge, and having a top passivation layer;

a metal layer formed directly onto a top outer surface of the passivation layer of the integrated circuit and located over a surface area of the integrated circuit that contains active circuitry, the metal layer defining a bottom electrode of a parallel plate capacitor, a landing pad for connection of a top electrode of the parallel plate capacitor, and a first trace connecting the bottom electrode to a first bond pad and a second trace connecting the landing pad to a second bond pad, the first and second bond pads being separately connected to the integrated circuit;

a gas sensitive dielectric layer covering exposed portions of the passivation layer and the metal layer, the gas sensitive dielectric layer having defined therethrough a via to the landing pad; and a porous top electrode on the gas sensitive dielectric layer and completely covering an area of the bottom electrode defined in the metal layer and filling the via in the gas sensitive dielectric layer to make electrical connection to the landing pad;

the integrated circuit being configured to output a signal indicative of a concentration of a gas responsive to determined capacitance of the gas sensitive dielectric layer.

15. The gas sensor of claim 14, wherein the integrated circuit is further configured to apply a voltage to the bottom electrode and measure charge displaced by the capacitive sensor through the top electrode.

16. The gas sensor of claim 14, wherein the gas sensitive dielectric layer is configured to cover the first trace and the second trace over an area larger than a maximum extent of the top electrode.

17. The gas sensor of claim 16, wherein the gas sensitive dielectric layer comprises a polymer.

18. The gas sensor of claim 14, wherein an area of the porous top electrode is larger than an area of the bottom electrode.

19. The gas sensor of claim 14, wherein the porous top electrode comprises a top surface exposed to an ambient environment.

20. The gas sensor of claim 14, further comprising output leads in communication with the integrated circuit for providing a signal with data indicative of a detected concentration of gas.

* * * * *